US010850066B2

(12) United States Patent
Uber, III et al.

(10) Patent No.: US 10,850,066 B2
(45) Date of Patent: Dec. 1, 2020

(54) CATHETERS AND RELATED EQUIPMENT

(71) Applicant: Bayer Medical Care Inc., Indianola, PA (US)

(72) Inventors: Arthur E. Uber, III, Pittsburgh, PA (US); Barry Lynn McDaniel, Pittsburgh, PA (US); David M. Griffiths, Pittsburgh, PA (US); Michael J. Bonnette, Minneapolis, MN (US); Eric J. Thor, Arden Hills, MN (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 104 days.

(21) Appl. No.: 14/627,242

(22) Filed: Feb. 20, 2015

(65) Prior Publication Data

US 2015/0165161 A1 Jun. 18, 2015

Related U.S. Application Data

(63) Continuation of application No. 13/660,790, filed on Oct. 25, 2012, now Pat. No. 8,961,491, which is a
(Continued)

(51) Int. Cl.
*A61M 25/01* (2006.01)
*A61M 5/00* (2006.01)
(Continued)

(52) U.S. Cl.
CPC ........ *A61M 25/0122* (2013.01); *A61M 5/007* (2013.01); *A61M 5/1408* (2013.01);
(Continued)

(58) Field of Classification Search
CPC ...... A61M 2025/0037; A61M 25/0075; A61M 25/007; A61M 2025/0076; A61M 2039/242; A61M 2039/2426
See application file for complete search history.

(56) References Cited

U.S. PATENT DOCUMENTS 3,384,089 A * 5/1968 Shriner ............. A61M 25/0075
137/527
3,474,786 A 10/1969 Spademan
(Continued)

FOREIGN PATENT DOCUMENTS

FR 2552332 A1 3/1985
GB 2040687 A 9/1980
(Continued)

OTHER PUBLICATIONS

The International Preliminary Report on Patentability dated May 7, 2015 from corresponding PCT Application No. PCT/US2013/061327.
(Continued)

*Primary Examiner* — Scott J Medway
(74) *Attorney, Agent, or Firm* — David Schramm; Joseph L. Kent; James R. Stevenson

(57) ABSTRACT

A catheter including at least one distal opening positioned at or near the distal end and at least one proximal opening near the proximal end and proximal to the at least one distal opening is described. The catheter may be configured for delivering at least a first fluid through the at least one distal opening to a central circulation system of a patient and delivering at least a second fluid through the at least one proximal opening to a peripheral circulation system of the patient.

17 Claims, 8 Drawing Sheets

Related U.S. Application Data continuation-in-part of application No. 12/297,637, filed as application No. PCT/US2007/066930 on Apr. 19, 2007, now abandoned.

(60) Provisional application No. 60/794,051, filed on Apr. 21, 2006.

(51) Int. Cl.
*A61M 5/14* (2006.01)
*A61M 25/00* (2006.01)
*A61M 25/06* (2006.01)

(52) U.S. Cl.
CPC ...... *A61M 25/003* (2013.01); *A61M 25/0075* (2013.01); *A61M 25/0113* (2013.01); *A61M 25/0606* (2013.01); *A61M 2025/0008* (2013.01); *A61M 2025/0175* (2013.01)

(56) References Cited

U.S. PATENT DOCUMENTS

| | | | | |
|---|---|---|---|---|
| 3,698,195 | A * | 10/1972 | Chapin | A01G 25/02 405/44 |
| 3,703,174 | A | 11/1972 | Smith | |
| 3,826,256 | A | 7/1974 | Smith | |
| 3,885,561 | A * | 5/1975 | Cami | A61M 25/007 137/493 |
| 3,888,249 | A * | 6/1975 | Spencer | A61M 25/0021 604/247 |
| 4,159,022 | A | 6/1979 | Pevsner | |
| 4,243,033 | A | 1/1981 | DeCaprio et al. | |
| 4,391,276 | A * | 7/1983 | Lazarus | A61M 25/007 604/266 |
| 4,403,985 | A | 9/1983 | Boretos | |
| 4,543,087 | A * | 9/1985 | Sommercorn | A61M 5/1582 604/264 |
| 4,549,879 | A * | 10/1985 | Groshong | A61M 25/0075 604/247 |
| 4,671,796 | A * | 6/1987 | Groshong | A61M 25/00 604/170.01 |
| 4,701,166 | A | 10/1987 | Groshong et al. | |
| 4,717,379 | A | 1/1988 | Ekholmer | |
| 4,753,640 | A * | 6/1988 | Nichols | A61M 25/003 604/247 |
| 4,961,731 | A * | 10/1990 | Bodicky | A61M 25/0041 604/264 |
| 4,968,306 | A * | 11/1990 | Huss | A61M 25/007 604/264 |
| 4,968,307 | A * | 11/1990 | Dake | A61M 25/007 604/264 |
| 5,009,636 | A * | 4/1991 | Wortley | A61M 25/007 604/43 |
| 5,030,210 | A * | 7/1991 | Alchas | A61M 25/0075 604/247 |
| 5,147,318 | A * | 9/1992 | Hohn | A61M 25/0075 604/174 |
| 5,147,332 | A * | 9/1992 | Moorehead | A61M 25/0075 604/247 |
| 5,163,921 | A * | 11/1992 | Feiring | A61M 25/0075 604/247 |
| 5,221,255 | A * | 6/1993 | Mahurkar | A61M 25/0028 604/43 |
| 5,224,938 | A * | 7/1993 | Fenton, Jr. | A61M 25/0075 604/247 |
| 5,250,034 | A * | 10/1993 | Appling | A61B 17/22 604/164.02 |
| 5,380,307 | A * | 1/1995 | Chee | A61M 25/0054 604/264 |
| 5,425,723 | A * | 6/1995 | Wang | A61M 25/007 138/114 |
| 5,626,564 | A * | 5/1997 | Zhan | A61M 25/007 604/164.01 |
| 5,643,228 | A * | 7/1997 | Schucart | A61M 25/007 604/264 |
| 5,662,619 | A * | 9/1997 | Zarate | A61M 5/158 604/246 |
| 5,772,636 | A | 6/1998 | Brimhall et al. | |
| 5,776,096 | A * | 7/1998 | Fields | A61M 25/0075 604/246 |
| 5,792,118 | A * | 8/1998 | Kurth | A61M 25/0017 604/246 |
| 5,800,408 | A * | 9/1998 | Strauss | A61M 25/007 137/625.47 |
| 5,817,057 | A | 10/1998 | Berenstein et al. | |
| 5,823,961 | A | 10/1998 | Fields et al. | |
| 5,928,203 | A * | 7/1999 | Davey | A61M 25/0075 137/848 |
| 5,935,120 | A * | 8/1999 | Williams | A61M 25/0026 604/500 |
| 5,957,901 | A * | 9/1999 | Mottola | A61M 25/007 604/264 |
| 6,001,069 | A * | 12/1999 | Tachibana | A61B 17/22012 601/2 |
| 6,113,577 | A | 9/2000 | Hakky et al. | |
| 6,179,813 | B1 * | 1/2001 | Ballow | A61M 25/0054 604/164.01 |
| 6,179,828 | B1 * | 1/2001 | Mottola | A61M 25/0075 604/256 |
| 6,280,423 | B1 * | 8/2001 | Davey | A61M 25/0021 604/264 |
| 6,442,415 | B1 | 8/2002 | Bis et al. | |
| 6,517,520 | B2 | 2/2003 | Chang et al. | |
| 6,536,437 | B1 * | 3/2003 | Dragisic | A61M 16/04 128/207.18 |
| 6,569,145 | B1 * | 5/2003 | Shmulewitz | A61B 17/12022 604/102.01 |
| 6,669,679 | B1 * | 12/2003 | Savage | A61M 25/007 604/131 |
| 6,929,633 | B2 * | 8/2005 | Evans | A61B 17/22 604/101.04 |
| 7,326,196 | B2 * | 2/2008 | Olsen | A61M 25/00 604/164.02 |
| 7,594,911 | B2 | 9/2009 | Powers et al. | |
| 7,618,411 | B2 | 11/2009 | Appling | |
| D609,338 | S | 2/2010 | Dozier, Jr. | |
| 7,713,239 | B2 | 5/2010 | Uber, III et al. | |
| 7,744,572 | B2 | 6/2010 | Bierman | |
| 7,901,395 | B2 | 3/2011 | Borden et al. | |
| 7,977,403 | B2 | 7/2011 | Lohrmann et al. | |
| 8,021,321 | B2 | 9/2011 | Zawacki | |
| 8,597,258 | B2 * | 12/2013 | Onuma | A61M 25/0075 604/247 |
| 2002/0187069 | A1 * | 12/2002 | Levin | A61M 1/34 422/44 |
| 2003/0093029 | A1 * | 5/2003 | McGuckin, Jr. | A61M 1/285 604/43 |
| 2004/0064086 | A1 * | 4/2004 | Gottlieb | A61B 5/14532 604/43 |
| 2004/0093061 | A1 | 5/2004 | Acosta et al. | |
| 2004/0097880 | A1 * | 5/2004 | Schur | A61M 25/007 604/164.01 |
| 2004/0167463 | A1 * | 8/2004 | Zawacki | A61M 1/3659 604/43 |
| 2004/0176743 | A1 * | 9/2004 | Morris | A61M 25/0075 604/537 |
| 2004/0193118 | A1 * | 9/2004 | Bergeron | A61M 25/0097 604/247 |
| 2005/0043703 | A1 * | 2/2005 | Nordgren | A61M 25/0075 604/500 |
| 2005/0054990 | A1 * | 3/2005 | Graft | A61M 25/0068 604/284 |
| 2005/0107738 | A1 * | 5/2005 | Slater | A61M 25/10 604/96.01 |
| 2005/0119597 | A1 * | 6/2005 | O'Mahony | A61M 1/3413 604/4.01 |
| 2005/0182352 | A1 * | 8/2005 | DiMatteo | A61M 25/003 604/43 |

(56) References Cited

U.S. PATENT DOCUMENTS

| | | | |
|---|---|---|---|
| 2005/0192558 A1* | 9/2005 | Bernard | A61M 25/007 604/525 |
| 2005/0277862 A1* | 12/2005 | Anand | A61M 25/0068 604/4.01 |
| 2006/0015068 A1 | 1/2006 | Amisar et al. | |
| 2006/0149191 A1* | 7/2006 | DiFiore | A61M 25/0075 604/246 |
| 2006/0253063 A1* | 11/2006 | Schweikert | A61M 25/003 604/30 |
| 2007/0161970 A1* | 7/2007 | Spohn | A61M 5/007 604/533 |
| 2007/0173777 A1 | 7/2007 | Murphy | |
| 2007/0213688 A1* | 9/2007 | Klein | A61M 5/158 604/523 |
| 2007/0225682 A1* | 9/2007 | Ash | A61M 25/003 604/532 |
| 2007/0232981 A1* | 10/2007 | Ravenscroft | A61M 25/003 604/6.16 |
| 2007/0293846 A1* | 12/2007 | von Oepen | A61M 25/0029 604/529 |
| 2008/0009804 A1* | 1/2008 | Rosetti | A61M 25/0029 604/173 |
| 2008/0097350 A1* | 4/2008 | Bell | A61M 25/0023 604/266 |
| 2008/0183141 A1 | 7/2008 | Reavill | |
| 2008/0197024 A1* | 8/2008 | Simpson | A61B 5/14542 205/778 |
| 2009/0048573 A1 | 2/2009 | Van Gompel et al. | |
| 2009/0118612 A1 | 5/2009 | Grunwald et al. | |
| 2009/0192451 A1* | 7/2009 | Mroncz | A61F 2/0013 604/99.02 |
| 2009/0240197 A1 | 9/2009 | Cowan et al. | |
| 2009/0254062 A1* | 10/2009 | McGlothlin | A61M 25/0015 604/508 |
| 2009/0318867 A1 | 12/2009 | Amisar et al. | |
| 2010/0049062 A1 | 2/2010 | Ziv | |
| 2010/0081986 A1* | 4/2010 | Matson | A61M 25/003 604/6.16 |
| 2010/0168642 A1* | 7/2010 | Appling | A61M 25/0068 604/6.16 |
| 2011/0087093 A1* | 4/2011 | Buiser | A61M 39/24 600/435 |
| 2011/0098653 A1 | 4/2011 | Powers et al. | |
| 2011/0112483 A1 | 5/2011 | Smith et al. | |
| 2011/0245806 A1 | 10/2011 | Patterson | |
| 2011/0270080 A1 | 11/2011 | Crane | |
| 2012/0209221 A1* | 8/2012 | Patterson | A61M 25/0021 604/284 |
| 2012/0323091 A1* | 12/2012 | Bennett-Guerrero | A61B 5/073 600/309 |
| 2015/0320976 A1* | 11/2015 | Maseda | A61M 25/02 604/508 |
| 2016/0184555 A1* | 6/2016 | Ishikawa | A61M 25/0026 604/528 |
| 2016/0220786 A1* | 8/2016 | Mitchell | A61M 25/0029 |
| 2019/0247630 A1* | 8/2019 | Brenizer | A61M 25/0075 |

FOREIGN PATENT DOCUMENTS

| | | |
|---|---|---|
| WO | 8101795 A1 | 7/1981 |
| WO | 9737715 A1 | 10/1997 |
| WO | 2001/13789 | 3/2001 |

OTHER PUBLICATIONS

"Baffle." Collins English Dictionary. Accessed online Jul. 29, 2013. <http://www.collinsdictionary.com/dictionary/english/baffle>.

"Check valve." Wikipedia. Accessed online Jul. 29, 2013. <https://en.wikipedia.org/wiki/Check_valve>.

"EPO Communication Extended European Search Report dated May 23, 2016".

"Machine Translation of FR2552332".

Karady, J., et al., "The effect of pacer bolus on contras media extravasation rate during coronary CT angiography examinations.", European Society of Radiology. Accessed online 2018.

Morden Peter. et al.,, "The Role of Saline Flush Injection Rate in Displacement of CT Injectable Peripherally Inserted Central Catheter Tip During Power Injection of Contrast Material", AJR, Jan. 2014, 202, W13-W18.

\* cited by examiner

CATHETERS AND RELATED EQUIPMENT

CROSS REFERENCE TO RELATED APPLICATIONS

This application is a continuation of U.S. application Ser. No. 13/660,790, filed Oct. 25, 2012, now U.S. Pat. No. 8,961,491, which is a continuation-in-part application of U.S. application Ser. No. 12/297,637 filed Oct. 17, 2008, which is a national phase application of International Application No. PCT/US07/66930 filed Apr. 19, 2007, and entitled "Central Venous Catheters and Related Equipment," which claims the benefit of U.S. Provisional Application No. 60/794,051, filed Apr. 21, 2006, the contents of all of which are hereby incorporated by reference in their entirety.

BACKGROUND

Catheters have long been used for injecting fluids into the central venous circulation. Needles and relatively short peripherally inserted venous catheters (PIVC) are used for routine blood draws and fluid administrations. Central catheters discharge fluids centrally in the venous vasculature, and are commonly used for administering drugs that are too damaging to the veins to administer peripherally, for example, some chemotherapy, antibiotics, and parenteral nutrition. If the catheter and/or the veins are large enough and strong enough, they can be used for the rapid injection of contrast agents for imaging procedures such as, for example, CT, MR, ultrasound, and molecular imaging studies. PIVC lines are generally inexpensive and can be placed or installed by normal nurses or in some cases by specially trained phlebotomists.

Longer central catheters and infusion ports are, generally, placed into veins in the chest or neck and usually require surgery to be inserted into the vein. More recently, long flexible catheters, generally referred to as peripherally inserted central catheters (PICC), have replaced infusion ports that are surgically implanted. These PICC lines can be inserted through a vein in the arm into the central venous circulation near the heart by trained nurses providing a more economic and patient friendly means for inserting a central catheter or infusion port. Generally, a guide wire is provided in the lumen of the flexible catheter to provide rigidity during the insertion procedure and a stiff needle, optionally with a dilator, is used to gain access to the vessel. The insertion procedure is carried out using a fluoroscope (or an ultrasonic imaging device) to help the user guide the catheter through the vessel into the central vena cava and to confirm proper placement of the catheter tip. Once in place, the needle or guide wire is removed, leaving the flexible catheter with the distal tip properly positioned for injection of fluid. These catheters can be left in place for days to months for the low flow-rate infusion of medication into the patient, and/or for sampling blood in patients with veins that have been compromised by disease or by the corrosive effects of chemotherapeutic drugs. The issues with PICC placement, phlebitis, and irritation or damage to the vessels and/or the heart have been made worse to some extent by the increased use of Power PICCs which can accommodate the pressures generated during the injection of CT contrast. This is because they often are made of a stiffer, stronger plastic and similarly may be larger in size to provide sufficient flow rates for the use in imaging procedures.

However, insertion of a PICC line has several challenges and drawbacks. The long, relatively stiff catheter and/or guide wire requires the creation and maintenance of a large sterile field around the insertion point so as to not contaminate the catheter or guidewire before insertion into the body. During insertion, the PICC line can catch on valves and tight bends in blood vessels, potentially causing trauma to blood vessels. In addition, because of the sometimes tortuous path of the veins, it can be difficult to move or remove the guidewire relative to the catheter during installation or when installation is complete. Similarly, a stiff tip on the PICC line can irritate a patient's heart if the PICC line is inserted too far, or damage the superior vena cava if not inserted far enough. If the catheter is too large or stiff, it can damage the peripheral vein through which it passes. This can lead to complications such as thrombosis, pain, and infection. Because of the importance of the correct placement of the catheter tip, the procedure was historically done under fluoroscopy in an interventional suite. At the location where the catheter exits the patient's skin, the stiffness of the catheter also increases the likelihood of motion and disruption of the seal between the catheter and the skin which can increase the possibility of infection.

BRIEF SUMMARY

The embodiments described herein provide one or more peripherally inserted central access catheters with one or more lumens which minimize trauma to the vessels. The controlled delivery of fluid may be used to help urge the catheter distally and/or to dilate the vein for easier insertion. Optionally it provides one or more proximally discharged lumens which optionally have the capability for accommodating the power injection for venous drug injections commonly used as part of an imaging procedure. Optionally the central access catheter can be inserted through an existing peripheral access device which can remain in place or be removed.

Some embodiments are directed to a catheter retention device that includes a catheter retention body having a proximal and a distal end, the catheter retention body defining a lumen designed and configured to receive a catheter; at least one distal lateral fitting on a distal portion of the catheter retention body, the lateral fitting being designed and configured to couple to a fluid source and introduce fluid into the distal portion of the lumen of the catheter retention body; and a distal fitting at a distal end of the catheter retention body, the distal fitting defining an aperture through which fluid and a catheter exit the lumen of the catheter retention body. In such embodiments, fluid flowing through the aperture may provide substantially all of the force required to expel the catheter from the catheter retention body.

Other embodiments are directed to a multi-port introducer including an introducer tube, designed and configured to be inserted into a blood vessel, the introducer tube having an opening with a diameter sufficient to accommodate a catheter and allow fluid delivery through the introducer tube during deployment of the catheter; a multi-port fitting head operably connected to the introducer tube; a first fitting operably connected to the multi-port introducer, the first fitting configured to provide a substantially straight path from a proximal opening of the first fitting to the opening in the distal end of the introducer tube; and one or more second fittings operably connected to a lateral portion of the multi-port introducer.

Still other embodiments are directed to methods for introducing a catheter into a blood vessel, the methods include the steps of introducing an angiocatheter into a blood vessel; and simultaneously introducing fluid and a catheter into the blood vessel.

BRIEF DESCRIPTION OF THE DRAWINGS

In the following detailed description, reference is made to the accompanying drawings, which form a part hereof. In the drawings, similar symbols typically identify similar components unless context dictates otherwise. The illustrative embodiments described in the detailed description, drawings, and claims are not meant to be limiting. Other embodiments may be utilized and other changes may be made, without departing from the spirit or scope of the subject matter presented herein. It will be readily understood that the aspects of the present disclosure, as generally described herein and illustrated in the Figures, can be arranged, substituted, combined, separated, and designed in a wide variety of different configurations, all of which are explicitly contemplated herein.

DETAILED DESCRIPTION

Figure 1:
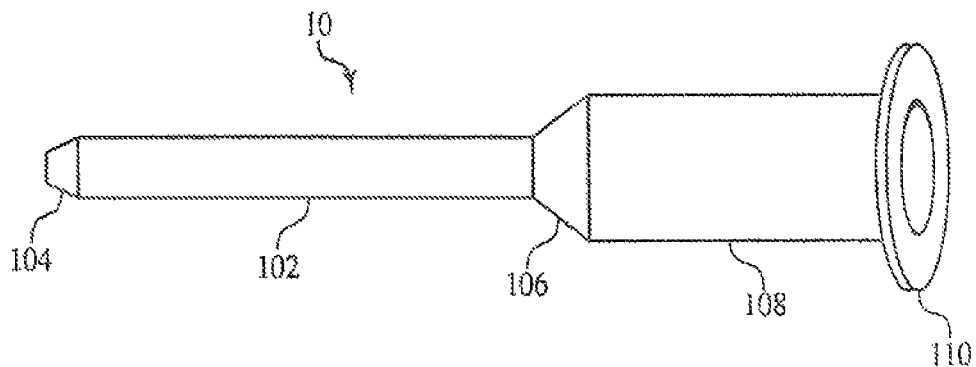
FIG. 1 is an illustration of an angiocatheter.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this document is to be construed as an admission that the embodiments described in this document are not entitled to antedate such disclosure by virtue of prior invention.

This disclosure is not limited to the particular systems, devices and methods described, as these may vary. The terminology used in the description is for the purpose of describing the particular versions or embodiments only, and is not intended to limit the scope.

The word "proximal" refers to a direction relatively closer to a clinician using the device described herein, and the word "distal" refers to a direction relatively further from the clinician. For example, the end of a catheter placed within the body of a patient is considered a distal end of the catheter, while the catheter end remaining outside the body is a proximal end of the catheter.

Embodiments of the present disclosure include devices useful for inserting a catheter into a blood vessel that provide for flow of fluid into the blood vessel simultaneously with insertion of the catheter. Simultaneous fluid flow with the insertion of a catheter allows the catheter to be carried into the blood vessel with the flow of fluid without need for a significant force from the back or distal end pushing the catheter into the blood vessel. In addition, the influx of fluid during insertion increases the blood volume in the blood vessel, expanding and opening the vein to facilitate insertion and centrally directed movement, and the flow rate of the blood through the vessel thereby providing sufficient blood flow to carry the catheter through the circulatory system without the need to provide a proximally directed force by distally pushing the catheter into the blood vessel. Once in the vessel, the catheter proceeds through the blood vessel at about the same rate as the flow rate of the blood or slower, so that there is a proximally directed force at the tip and optionally over much of its length caused by drag as the fluid moves past the catheter, reducing the likelihood of kinking that can happen when the catheter exceeds the velocity of the blood and the body of the catheter pushes past the tip during insertion.

The need for guidewires and other stiffening means associated with the catheter during insertion is also reduced or eliminated as well as allowing catheters to be prepared from softer or more flexible materials such as silicones or softer polyurethanes, or have smaller outside diameter and thinner walls than is possible using catheters and methods of the prior art. Reducing or eliminating the need for guidewires also allows for the use of coated or multi-layer catheter tubes. For example, in certain embodiments, the catheter may be coated or include a layer of hydrophobic drugs on the inner surface of the catheter while the outer surface can be chosen from materials that are compatible with the blood or that include, for example, a coating of anti-coagulant or anti-fibrotic drug Eliminating guidewires also allows for variation in the inner and outer diameter and variation in the material stiffness over the length of the catheter. For example, in some embodiments, the diameter of the catheter may be decreased relative to the body of the catheter to reduce the likelihood of trauma caused by the tip or to reduce the total volume of fluid in the lumen.

Additional embodiments are directed to catheters having a variety of new features, catheter retaining devices that allow coiled catheters to be contained within a shortened sterile housing before, during, and after insertion of the catheter into the blood vessel, and methods for using the insertion devices, catheters, and catheter retaining devices. Various such embodiments may allow for a reduced sterile field size, enable accurate tip placement by making it easier to adjust the location of the catheter tip in both upstream and downstream directions, and reduce the need for cutting of the catheter to the appropriate length before insertion into the vein.

The devices of various embodiments include a means for introducing fluid into the blood vessel while simultaneously inserting a catheter into a blood vessel. Means for introducing fluid into a blood vessel are well known and used in the art. For example, short peripherally inserted catheters, angiocatheters, are commonly used to introduce intravenous (IV) fluids into a blood vessel. As depicted in FIG. 1, such angiocatheters 10 generally include a short insertion tube 102 having an angled, conical, or tapered distal end 104, and a Venturi feature or other tapered portion 106 that connects the short insertion tube 102 to a body 108. The body 108 generally includes a proximal fitting 110 that allows the angiocatheter 10 to be connected to tubing associated with a fluid source such as an IV bag or syringe for infusion of a drug or other agent. A needle, not shown, extends through the lumen of tube 102 and is use to puncture the skin, tissue and blood vessel wall. Once in the vessel, the tube 102 is pushed over the needle into the vessel and the needle is withdrawn and discarded.

Certain embodiments of the present disclosure include catheter retaining devices that are configured to attach to the fitting of angiocatheters or short peripherally inserted venous catheters (PIVC) like the angiocatheter 10 illustrated in FIG. 1. The ability to deliver a longer catheter through an existing angiocatheter without having to make a new IV stick may provide a benefit in some emergency and critical care situations or in patients where finding a vein is difficult.

Figure 2A:
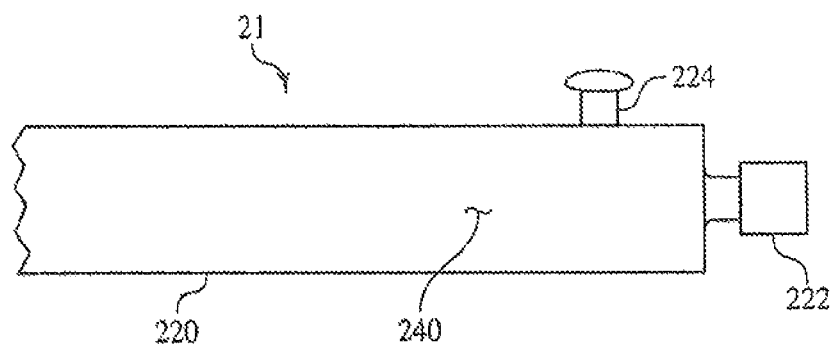
FIG. 2A is an illustration of a catheter retention device.
Figure 2B:
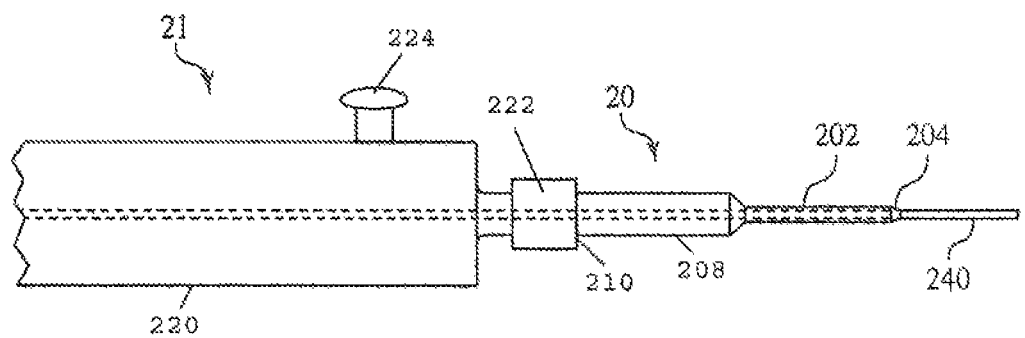
FIG. 2B is an illustration of a catheter retention device attached to an angiocatheter.

As illustrated in FIG. 2A, such catheter retaining devices 21 may include a catheter retention body 220 having a lumen sized and shaped to hold a central catheter 240, a distal fitting 222 configured to attach to the fitting of an angiocatheter, and one or more lateral fittings 224 configured to attach to a fluid source. In some embodiments, the lateral fitting 224 may be at a distal portion of the catheter retention body 220. FIG. 2B shows the catheter retaining device 21 attached to a common angiocatheter 20. In operation, fluid may enter the catheter retention body 220 through the lateral fitting 224. The air in the catheter retaining body 220 can exit through distal fitting 222 prior to being connected to the angiocatheter 20. After air has been removed and fluid has accumulated in the catheter retention body 220, it can be connected to angiocatheter 20, and the fluid will flow through the distal fitting 222 into the angiocatheter 20 through the proximal fitting 210 and the angiocatheter body 208. The fluid will exit the angiocatheter 20 and enter the blood vessel through the distal end 204 of the insertion tube 202. The flow of fluid through the devices will provide a pulling force on the catheter 240 related to the velocity or flow rate of the fluid flow. As the rate increases, the force will be sufficient to overcome the static friction holding the catheter in place and begin drawing the catheter from the catheter retention body 220 and into the blood vessel where blood flow enhanced by the additional fluid from the device will carry the catheter through the circulatory system to the site of deployment.

Figure 3A:
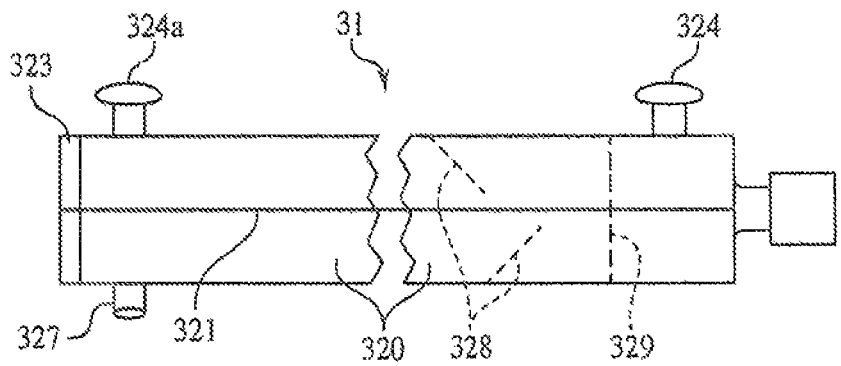
FIG. 3A is an illustration of a catheter retention device showing the location of exemplary fittings.

The catheter retaining devices of various embodiments may include any number of additional features necessary to control flow of fluid through the device, remove unwanted air or fluid from the central lumen of the catheter retention body 220, control deployment rate or velocity of the catheter 240, and direct the catheter through the catheter retaining device. For example as illustrated in FIG. 3A, in some embodiments, the catheter retaining device 31 may include one or more lateral fittings in addition to the distal lateral fitting 324 located along the catheter retention body 320, and in certain embodiments, a second lateral fitting 324a may be positioned on a proximal portion of the catheter retention body. In such embodiments, the second lateral fitting 324a may provide an additional means for introducing fluid into the catheter retention body 320. Alternatively or in addition, the second lateral fitting 324a may be on a distal portion of the catheter retention body 320 or the angiocatheter body so that fluid flowing through it exerts little or no force on the catheter while in the catheter retention body 320 or the angiocatheter body and flows into the vessel to distend and/or augment the flow in the vessel. The second lateral fitting may further provide a means for allowing air or fluid from within the catheter retention body 320 to leave the lumen as fluid enters through the distal lateral fitting 324. In some embodiments, the catheter retaining device 31 may further include one or more one-way purge vents 327 that are capable of allowing air and fluid to exit the catheter retention body 320.

Figure 3B:
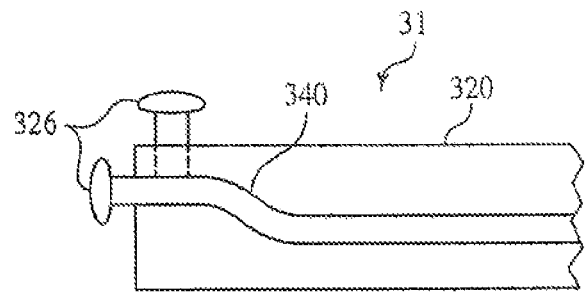
FIG. 3B is an illustration of a catheter retention device showing the location of exemplary fittings and valves.

The proximal portion of the catheter retention body may further include one or more fittings associated with the catheter. For example, as illustrated in FIG. 3B, in some embodiments, the catheter 340 may terminate at a catheter fitting 326 provided at a proximal portion of the catheter retention body 320. The catheter fitting 326 may provide a means for introducing fluids into the catheter 340 for delivery to the patient. As the catheters 340 of various embodiments may have more than one lumen, a separate catheter fitting may be provided for each lumen of the catheter 340. Thus, the catheter retaining device 320 of embodiments may have one, two, three, or more catheter fittings 326 disposed on a proximal portion of the catheter retention body 320.

In some embodiments, the catheter retaining device 31 may further include one or more valves positioned to regulate the flow of fluid into and out of the catheter retention body 320. For example, in some embodiments, a valve may be positioned at the distal lateral fitting 324, and in other embodiments, a valve may be positioned at the catheter fitting 326. In still other embodiments, the catheter retaining device 31 may include a valve at both the distal lateral fitting 324 and the catheter fitting 326. In still other embodiments, the catheter retaining device 31 may include additional valves located anywhere along the catheter retention body 320. For example, valves may be provided with additional lateral fittings or valves may be associated with catheter fittings. The valves of various embodiments may be any type of valve known in the art including, for example, gate or slide valves, needle valves, check valves, diaphragm valves, butterfly valves, and like. These valves can be manually controlled or automatically controlled by the injection system to optimize the flow of fluid to and through catheter retention body 320 as well as the blood vessel to provide deployment force to the catheter as the catheter proceeds into veins as well as to ease movement to the central circulation.

In certain embodiments, the catheter retention body 320 may include texturing or features on an inner surface. Examples of such texturing include helical, longitudinal, circumferential grooves, rifling, projections, or other texturing. Texturing may allow a portion of an outer surface of the catheter to contact a portion of an inner surface of the catheter retention body 320 to maintain the position of the catheter in the lumen of the catheter retention body 320 and to provide friction to hold the catheter in place while allowing movement when acted on with sufficient force. In some embodiments, texturing or features may be provided to regulate and direct the flow of fluid through the catheter retention body 320 when the catheter is placed within the lumen of the catheter retention body 320. For example, rifling of the inner diameter of the catheter retention body 320 may allow for directed flow of fluid within the second catheter around the catheter.

In particular embodiments, the catheter retention body 320 may include internal features such as, for example, one or more bulkheads 329 or baffles 328 positioned at intervals that segment portions of the catheter retention body 320 or provide currents that can provide additional pulling force on the catheter. In other embodiments, the baffles or bulkheads may be positioned to aid in the movement of the catheter through the catheter retention body by, for example, ensuring that the catheter is centered within the catheter retention body as it moves through the catheter retention body. In still other embodiments, the baffles or bulkheads may be positioned to aid in packaging of the catheter in the catheter retention body.

In certain embodiments, the catheter retaining device 31 may include a centering mandrel 321 sized to be received within a lumen of the catheter and a mandrel clamp 323 positioned to hold the centering mandrel at the center of a circumference of the catheter retention body 320. In some embodiments, the centering mandrel 321 may be movably received by the mandrel clamp 323 such that the centering mandrel 321 may enter the catheter retention body 320 and be retained therein as the catheter progresses through the blood vessel.

There are several potential benefits to the inclusion of a centering mandrel 321. It allows for a reduced flow rate of fluid necessary to introduce the catheter into the blood vessel by reducing the friction of the catheter on the catheter retention body 320 inner wall. The centering mandrel 321 positions the catheter such that an approximately equal amount of fluid flows on either side of the catheter, thereby optimizing the amount of insertion force exerted on the catheter by the fluid. The centering mandrel may also reduce the tendency of the catheter to bend or kink. A similar effect may be obtained by providing additional fluid deployment ports around the circumference of the deployment tube. Thus, lowered required flow rates may allow for hand-operated syringes to provide adequate fluid flow to insert the catheter into a patient. The centering mandrel may also provide some controlled friction to limit the rate of deployment by sizing of the fit or geometry. To fit within the catheter, the centering mandrel 321 may be smaller in diameter than the inner diameter of the catheter. For example, when used with a second catheter having an inner diameter of about 0.008 inches to about 0.035 inches or about 0.01. In this example, the centering mandrel 321 may have a diameter of about 0.008 inches or less.

Figure 4A:
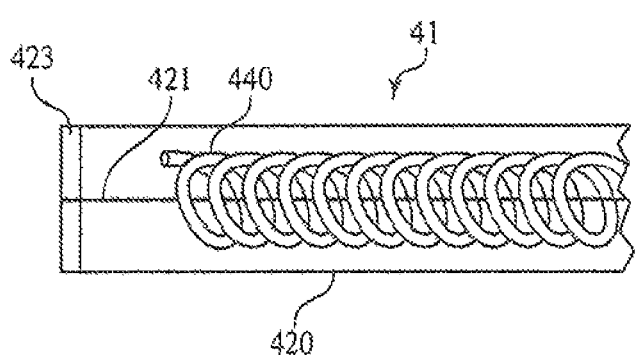
FIG. 4A is an illustration showing a catheter retention device having a catheter wound within the lumen.

As illustrated in FIG. 4A, the catheter retention body 420 may be designed to receive and package the catheter in any number of ways. For example, in some embodiments, the centering mandrel 421 may be fixedly received by the mandrel clamp 423, and the catheter 440 may be wound around the centering mandrel 421. When wound around the centering mandrel 421, the catheter may be in a single coiled, double coiled, or triple coiled configuration. The centering mandrel 421, in such embodiments, may provide for improved packaging of the catheter 440 that may allow for the size of the catheter retention body 420 to be reduced thereby reducing the overall size of the catheter retaining device 41.

Figure 4B:
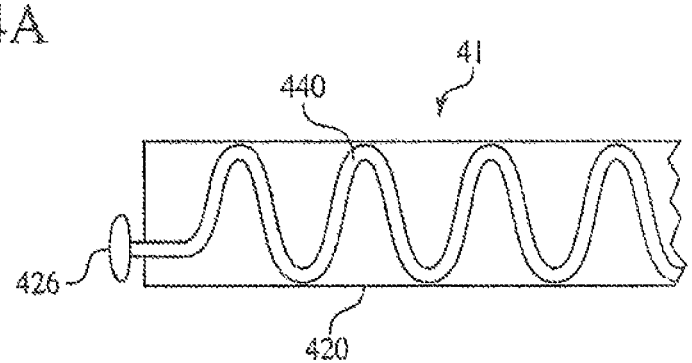
FIG. 4B is an illustration showing a catheter retention device having a catheter folded within the lumen.
Figure 4C:
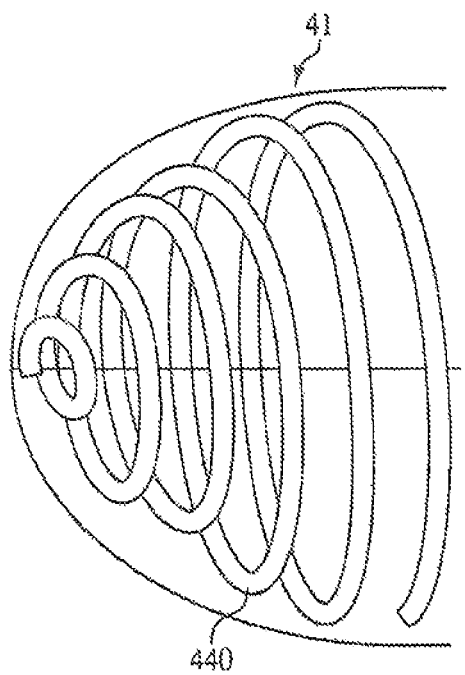
FIG. 4C is an illustration showing a catheter retention device having a catheter wound in a spherical catheter retention device.
Figure 4D:
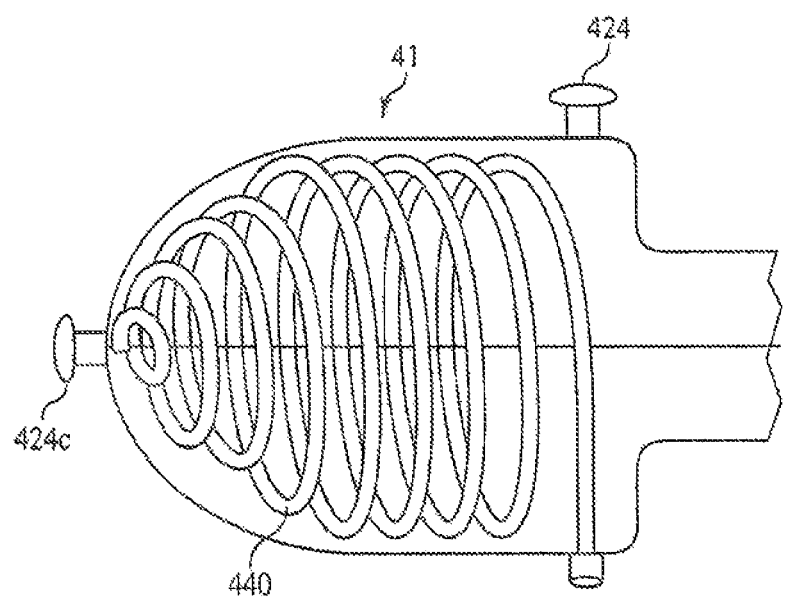
FIG. 4D is an illustration showing a catheter retention device having a catheter wound in a spherical catheter.

While the fixed centering mandrel 421 provides a means for winding or coiling the catheter 440 in the catheter retention body 420, in some embodiments, the catheter may be wound or coiled in the catheter retention body 420 without a centering mandrel. In other embodiments, the catheter may be folded in the catheter retention body 420 as illustrated in FIG. 4B. The shape of the catheter retention body 420 may reflect the means by which the catheter is stored within the catheter retention body 420. For example, in embodiments in which the catheter is coiled or wound the catheter retention body 420 may have a substantially cylindrical, conical, or spherical shape, and in embodiments in which the catheter is folded, the catheter retention body 420 may have a square or rectangular box shape. Coiling the catheter on the inner surface of the catheter retention body 420 and pulling it off the inner surface may provide a compact, low friction deployment mechanism. In other embodiments, as illustrated in FIG. 4C and FIG. 4D the catheter 440 may be coiled upon itself, similar to a ball of twine that can be unwound from the inside out and the catheter retaining device 41 may have a substantially spherical FIG. 4C or oblong FIG. 4D shape.

Because the catheter 440 can be wound, coiled, or folded within the catheter retention body 420, the size of the catheter retention body may be compacted, i.e., shortened in length and larger in diameter thereby improving the hand ability of the catheter and catheter retention body. For example, in embodiments in which the catheter is not wound or coiled, the catheter retention body may have a length substantially equal to the length of the catheter, for example, from about 20 cm to about 70 cm or about 25 cm to about 65 cm and a diameter sufficient to receive a 4 French, 5 French, 6 French, or 7 French catheter. For example, the catheter retention body may have a lumen having an internal diameter of from about 1.5 mm to about 5 mm or about 2 mm to about 4 mm. In embodiments in which the catheter is wound or coiled within the catheter retention body, the length of the catheter retention body 420 may be substantially shortened while the diameter of the catheter retention body 420 may be increased. For example, length L of a cylindrical catheter retention body 420 may be about 5 cm to about 50 cm for a 4 French, 5 French, 6 French, or 7 French catheter having a length of about 20 cm to about 70 cm, and in other embodiments, the cylindrical catheter retention body 420 may have a length of about 10 cm to about 40 cm, about 15 cm to about 35 cm, or about 20 cm to about 30 cm, or any individual value within these exemplary ranges. Such cylindrical catheter retention bodies 420 may have an internal diameter D of about 10 mm to about 20 cm, about 50 mm to about 10 cm, or any individual value within these exemplary ranges. Similar sizes can be achieved for catheter retention bodies 420 that have square or rectangular box shapes. For example the length of a rectangular box shaped catheter retention body may be about 10 cm to about 40 cm, about 15 cm to about 35 cm, or about 20 cm to about 30 cm, or any individual value within these exemplary ranges, and the rectangular box shaped catheter retention body may have a height and width, which can be equal or different, of about 10 mm to about 20 cm, about 50 mm to about 10 cm, or any individual value within these exemplary ranges.

In some embodiments, the catheter may be introduced into the blood vessel using only the flow of fluid through the catheter retaining device 41 and/or the introducer. In other embodiments, the catheter retention device may further include a means for manually or automatically reeling the catheter out of the catheter retention body and/or reeling the catheter back into the catheter retention body as may be useful during the procedure to provide for optimal final tip placement. For example, a handle may be disposed on an outer surface of the catheter retention body that may facilitate winding or unwinding of the catheter around a spindle inside of the catheter retention body 420, and in other embodiments, a motor or motorized wheel, which can be operated manually or by an injection controller, may facilitate winding or unwinding of the catheter within the catheter retention body 420. The means for reeling in and reeling out the catheter may allow the deployed catheter to be retracted, repositioned, or replaced without sacrificing sterility because the catheter will remain enclosed within the catheter retention body throughout the procedure. In other embodiments, the catheter retention body 420 may include one or more friction augmentation devices such as, for example, a pinch valve, iris, or other compression device that can be pulsed to control the feed-out of the catheter during insertion. Such friction augmentation devices can be controlled manually or by a system controller.

The catheters 440 contained within the catheter retention body 420 may be any type of catheter known in the art. For example, the catheters may include one or more lumens and can be configured as 4 French, 5 French, 6 French, or 7 French catheters. In certain embodiments, flow insertion and flow augmentation may allow for catheters having a small diameter, 1 French, 2 French, 3 French or as small as PE-10 tubing to be inserted. Such catheters can be configured to deploy any materials known in the art such as, for example, saline, active agents, drugs, medication, nutrients, or other foodstuffs. In some embodiments, the catheter may include a guidewire or other stiffening means that can be used during deployment of the catheter and then removed during use. In particular embodiments, catheters contained within the catheter retention body may not need to include a guidewire or stiffening means. Without wishing to be bound by theory, the increased blood volume created by the simultaneous administration of fluid during introduction of the catheter 440 may allow the catheter to be deployed without pushing the catheter into the blood vessel from its proximal end. Alternatively, the amount or amplitude of the primal pushing force can be reduced, while allowing for manual control by the nurse, providing a "power assist" for the catheter insertion procedure. The catheter is carried to the deployment site by the flow of blood which can be augmented by the flow of fluid and is less likely to kink as a result of portions of the catheter being pushed past the distal end of the catheter. As such, the need for stiffening means is reduced or eliminated, and moreover, in some embodiments, softer and more compliant materials may be used to make the catheter. In addition the vessels are dilated or enlarged by the augmented flow, thereby making insertion easier, less traumatic, and less problematic. Taken together, these improvements provide a catheter introduction system that is less likely to cause injury to the blood vessel.

Figure 5:
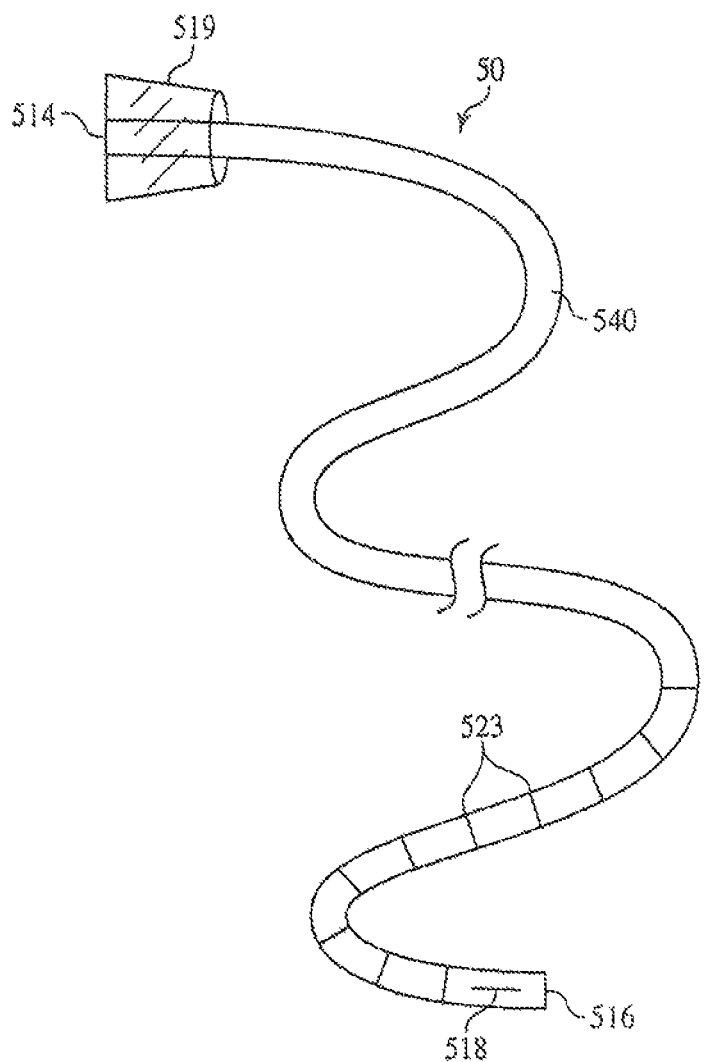
FIG. 5 is an illustration showing an exemplary catheter.

As illustrated in FIG. 5, the catheter 540 incorporated into the catheter retaining devices described above may include features to facilitate insertion and/or facilitate interactions with the catheter retention device. Generally, the catheter 540 may have a distal end 516 configured to be inserted into a blood vessel, and a proximal end 514 that may include at least one opening (not shown) capable of allowing fluid to flow into and through the catheter 540 into the patient's vein. The proximal end 514 of the catheter 540 may be designed and configured to interact with an inner surface of the catheter retention body. For example, in some embodiments, a bulge or stopper 519 fixedly attached to the catheter may be provided at the proximal end of the catheter 540. The bulge or stopper 519 may have any shape. For example, in some embodiments, the bulge or stopper 519 may be round or cylindrical, and in certain embodiments, the bulge or stopper 519 may have a cone shape. The bulge or stopper 519 may be sized to stop the second catheter 540 at an appropriate position within the catheter retention body to ensure that the catheter does not flow past the deployment site or completely enter the patient's blood vessel. Thus, in some embodiments, the bulge or stopper 519 may be sized to approximately equal the inner diameter of the catheter retention body and have a larger diameter than the distal fitting of the catheter retention body such that forward movement of the catheter 540 is stopped when distal fitting is reached.

In some embodiments, the catheter 50 may include marking features 523 spaced along the length of the catheter. Such marking features may show the length of the catheter and can be placed at equally spaced intervals such as, for example, each centimeter, each inch, or any suitable unit of measure known in the art. The markings 523 may provide a means for quickly customizing the length of the catheter 50 by cutting the catheter before it is introduced into the patient. In certain embodiments, the length of the catheter 50 may be determined before the catheter is packaged in, for example, a catheter retention body, to avoid cutting of the catheter during the introduction procedure. Because the catheter retention body is sterile, the sterility of the catheter is maintained while the catheter is in the catheter retention body; avoiding cutting eliminates the possibility of contamination during the introduction procedure. Alternatively, the catheter may have a standard length and extra catheter can be pulled back and stored in the catheter retention body providing another means for avoiding cutting during the introduction procedure and potentially contaminating the catheter before introduction. Having markings extending towards or to the proximal end of the catheter can help in ascertaining that the correct length of catheter has been inserted into the patient.

Figure 5A:
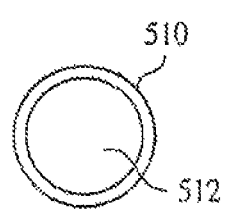
FIG. 5A is an illustration of a cross-section of a single lumen catheter.
Figure 5B:
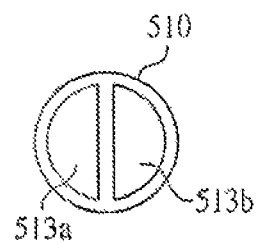
FIG. 5B is an illustration of a cross-section of a double lumen catheter.

Some embodiments of the present disclosure are directed to catheters. Such catheters 50 generally include an elongated, unitary, tubular structure made of a flexible, biocompatible material, such as silicone rubber, that include a cylindrical wall 510 defining a longitudinal bore or lumen 512, as illustrated in FIG. 5A. In some embodiments, the catheter 50 may include two or more longitudinal bores to provide multiple lumen catheters, and in particular embodiments the catheter may include two adjacent bores, which may have a substantially "D" shape 513a, 513b, as illustrated in FIG. 5B. The catheters 50 of various embodiments may be sized to have a conventional diameter for catheters designed for insertion into blood vessels. For example, the catheters of embodiments may be 1 French, 2 French, 3 French, 4 French, 5 French, 6 French, or 7 French sized catheters having external diameters of about 0.6 mm to about 2.5 mm, or very thin tubing, such as PE10. The diameter of the lumen may vary based on the thickness of the sidewalls and the number of lumen associated with the catheter.

In some embodiments, the one or more lumens may extend throughout the length of the catheter 50, and the catheter 50 may have at least one proximal opening 514 and at least one distal opening 516 through which fluids can flow into and out of the catheter 50. In other embodiments, the one or more lumens may terminate before the end of the catheter. For example, in some embodiments, the catheter may have a proximal opening 514 and a sealed or otherwise closed distal end 516, and the lumen may open to the blood vessel by one or more lateral slits 518 in the cylindrical wall 510 of the catheter 50 to provide a lateral opening. Such slits 518 may allow the opening to be created when fluid is introduced into the lumen 512, 513a, or 513b, and fluid pressure within the lumen may force the lateral slit 518 to open allowing fluid to exit the catheter. When the flow of fluid is stopped and fluid pressure within the lumen is decreased, the slit 518 may close keeping blood or other fluids from entering the catheter when fluid is not being introduced into the catheter 50. Similarly, applying suction to the catheter will open the slit and allow blood to be drawn into the catheter for sampling as needed. A non-limiting example embodiment is a Groshong catheter.

Figure 6:
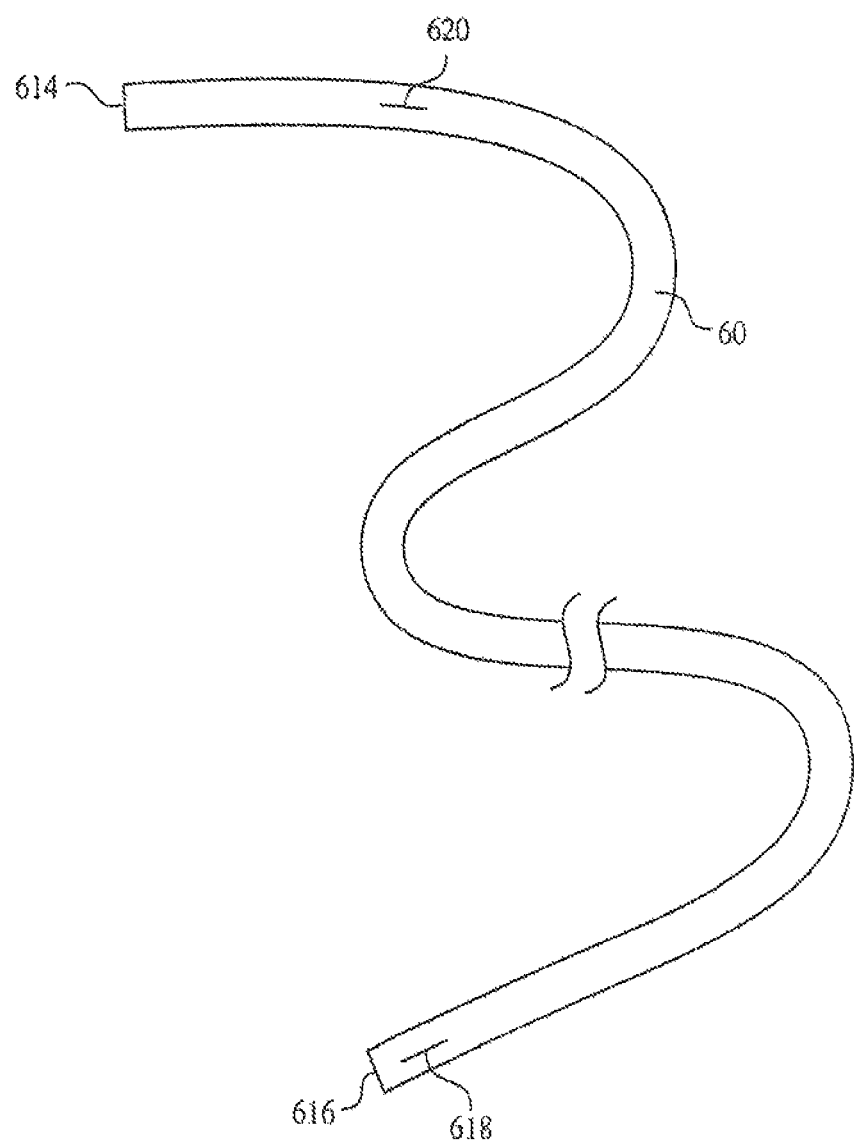
FIG. 6 is an illustration of a catheter showing the locations of exemplary lateral slits.

In certain embodiments, a multi-lumen catheter 50 such as the catheter illustrated in FIG. 5B may include more than one lateral slit. For example, as illustrated in FIG. 6, catheter 60 may include a distal lateral slit 618 at or near a distal end of the catheter 60, and one or more additional lateral slits 620. In some embodiments, the additional lateral slit 620 may be positioned at or near a proximal end 614 of the catheter 60. In other embodiments, additional lateral slits 620 may be positioned at one or more positions throughout the length of the catheter 60. In particular embodiments, the catheter 60 of such embodiments may be a multi-lumen catheter having at least two lumens such as the exemplary catheter illustrated in FIG. 5B. The distal lateral slit 618 may be associated with a first lumen 513a, and the one or more additional lateral slits 620 may be associated with a second lumen 513b. Thus, for example, the first lumen 513a may be configured to transport an active agent to the distal end 616 of catheter 60, while the second lumen 513b is configured to transport a second active agent for more proximal administration. In some embodiments, the second lumen 513b having a proximal additional lateral slit 620 may be configured to transport medical fluid or saline that can be introduced into the blood vessel during introduction of the catheter 60 into the blood vessel, and the additional saline may act to speed blood flow through the blood vessel and aid in the movement of the catheter 60 through the blood vessel. In embodiments in which the catheter 60 includes two or more additional lateral slits 620 configured to transport medical fluid, medical fluid may be released over the entire length of the catheter during introduction of the catheter 60 into the blood vessel. The combined local effects of each additional lateral slit may allow for improved blood flow by increasing blood volume from the site of insertion of the catheter 60 to the final deployment site. Holes or slits positioned along the body of the catheter 60 or at a distal end 616 of the catheter 60 may allow fluid flow within the vessel to expand the vessel and ease insertion of the catheter 60 during insertion. After introduction of the catheter 60, medical fluid may continue to be administered through the additional lateral slits 620, or fluid flow may be stopped, and in some embodiments, active agents, drugs, medication, nutrients, or other foodstuffs may be administered to the patient through the second lumen 513b and additional lateral slits 620. A proximal slit or opening may be used to deliver CT contrast and prevent rupture if softer materials or smaller diameters are used. In some embodiments, the separation of the proximal and the distal ports may be sufficient to provide central vascular access for slow or moderate flows through a more atraumatic catheter section or segment and enable proximal access in a more peripheral vessel for higher or power injected flows.

In some embodiments, the catheter 60 may have a single lumen that has one or more distal slits or openings for distal delivery and/or withdrawal as well as normally closed proximal slits or holes for delivery of drugs at a high rate or pressure which the lumen could not sustain over its whole length. In some embodiments, the catheter may have two or more slits arranged proximally. The dimension of the slits and catheter material stiffness, diameters, and the thickness of the walls are selected such that they do not open inward under vacuum when blood is being sampled or under moderate pressures, such as when drugs are being infused slowly, but do open under pressures and flow rates that are needed for power injections and would cause a rupture of the catheter unless that flow were diverted or released into the vessel. If the properties are selected so that the catheter swells controllably under the designed pressure, this opens the slits even further and enables increased flow. The geometry and properties of the slits and the catheter determine the opening pressure, and the number of slits determines the flow rates that can be accommodated at a given pressure. This embodiment can be used with any existing or novel methods of insertion, sterile field establishment and other procedural aspects to limit the need for the majority of the catheter length to experience high pressures when injecting at high flow rates.

In some embodiments, the catheter 50, 60 may have additional coatings such as, but not limited to, antibacterial coatings, anti-fibrotic coatings, or other coatings that can facilitate sterility, ease of introduction into the blood vessel, or long-term use in the patient. In some embodiments, the catheter may be coated with a component or layer provided to stiffen the catheter 50, 60, and in certain embodiments, at least one longitudinal bore of the catheter may include a guidewire or other stiffening means removably inserted into the longitudinal bore. Such a guidewire or stiffening means may provide ease of handling of the catheter 50, 60 during introduction into the blood vessel, and in some embodiments, the guidewire or stiffening means may be removed after deployment of the catheter 50, 60. In other embodiments, the catheter may not include a guidewire or stiffening means. For example, in embodiments in which the catheter 60 includes a distal lateral slit 618 at a distal end 616, fluid pressure within the catheter created while the lateral slit is closed may reduce or eliminate undulating, flapping, or whipping of the catheter 60 during deployment of the catheter, even for single lumen catheters. Similarly, in multi-lumen catheters, a first lumen 513a may be configured to accept and deploy fluid through a distal port, and a second lumen 513b may be sealed and configured to accept a fluid that is not delivered to the patient, or may have a very small distal opening so that high pressure is developed at modest flow rates. In such embodiments, fluid pressure within the second lumen 513b may sufficiently stiffen the catheter 50 so as to reduce or eliminate the need for guidewires or other stiffening means.

The geometry and shape of the catheter body may be designed to withstand pressure by incorporating multiple design factors, for example, burst strength of the material and incorporation of reinforcing materials. To achieve the high flow rates for injecting contrast for imaging procedures utilizing pressure injections, the catheters need to be capable of withstanding higher pressures, e.g., 300 psi or 325 psi, making these catheters stiffer than catheters that are used for the lower flow rates required for medication infusion and blood withdrawal, e.g., about 10 psi to about 100 psi. In some embodiments, a distal portion of the catheter may be composed of a first material at a proximal end of the catheter capable of withstanding pressures up to 350 psi, or about 300 psi to about 325 psi, and a more flexible second material capable of withstanding pressures up to 100 psi, or from about 10 psi to about 100 psi. In other embodiments, the catheter may be composed of a single material but may be designed to include a first portion at a proximal end of the catheter having a wall thickness that is greater than a distal portion of the catheter. The greater thickness may allow the proximal portion of the catheter to withstand higher pressures than the distal end of the catheter. Typically, the wall thickness may allow the proximal end to withstand high pressures than the distal end of the catheter.

Figure 7:
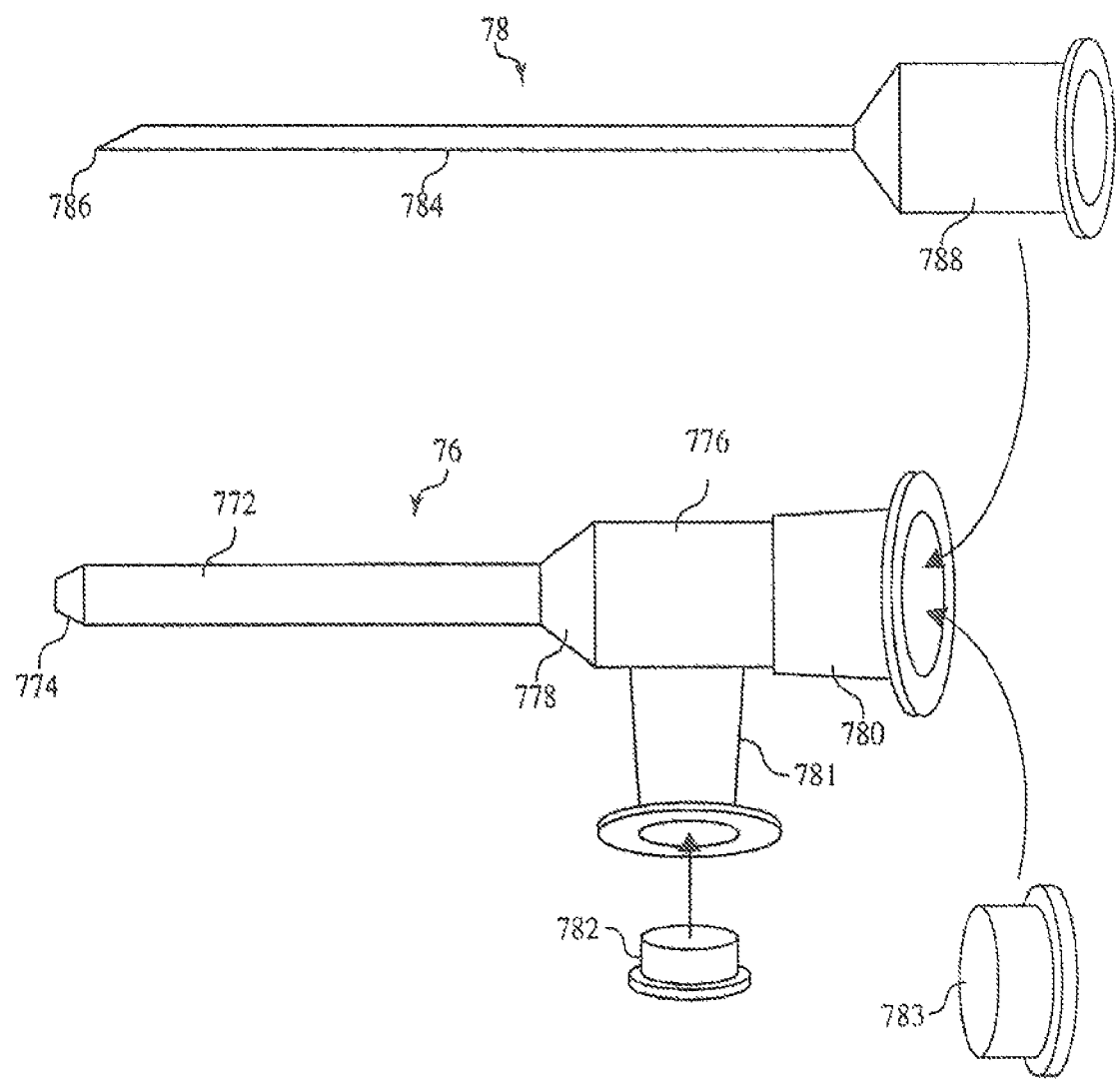
FIG. 7 is an illustration of a multi-port introducer and a needle deployment device.

Further embodiments are directed to multi-port introducers and catheter retention devices designed to be used in conjunction with multi-port introducers. FIG. 7 shows an exemplary multi-port introducer 76 that includes an introducer tube 772 having a tapered distal end 774 designed to be introduced into a blood vessel. The proximal end of the introducer tube 772 may be operably connected to a multi-port fitting head 776, which may include one or more fittings or ports for connecting with other apparatuses and devices. In FIG. 7, two fittings are provided 780 and 781. The introducer tube 772 may be connected to the multi-port fitting head 776 by any means. For example, the multi-port fitting head 776 may be an integral part of the introducer tube 772 and, therefore, may be molded with the introducer tube 772. In other embodiments, the multi-port fitting head 776 may be molded separately and fixedly attached to the introducer tube 772 using, for example, an adhesive, one or more connectors, or any other connector means known in the art or combinations thereof. In some embodiments, the introducer tube 772 and/or the multi-port fitting head 776, or portions thereof, may include one or more Venturi features 778.

The introducer tube 772 may have any inner diameter sufficiently sized to accommodate the catheter. For example, the introducer tube 772 may have an inner diameter sufficient to accommodate a 4, 5, 6, or 7 French catheter. In some embodiments, the introducer tube 772 may be an 18 gauge catheter having an inner diameter of about 0.051 inches. In some embodiments, the introducer tube 772 may be sized such that the lumen and opening in the distal end 774 of the introducer tube 772 provide sufficient space to allow fluid delivery through the introducer tube 772 during deployment of the catheter. Thus, fluid delivery can occur simultaneously with deployment of the catheter. In other embodiments, the distal end 774 of the introducer tube 772 may be sized to fit snuggly around the catheter during deployment, and simultaneous fluid deployment may be carried out through one or more holes or apertures in the introducer tube 772 that are positioned to allow fluid to flow from the introducer tube 772 into the blood vessel while the catheter is being deployed.

In some embodiments, the multi-port introducer 76 may include a Venturi feature 778 disposed between the multi-port fitting head 776 and the introducer tube 772 that is designed and arranged to interact with the catheter during deployment of the catheter. The Venturi feature 778 may generally have a substantially conical shape which is sized and configured to reduce the inner diameter of the multi-port fitting head 776. In addition, the Venturi feature may be designed to increase the velocity of the fluid and thus the force pulling on the catheter into the vein or reduce drag caused by the flow of fluid and friction created when the catheter contacts an inner surface of the Venturi feature 778 during insertion.

The multi-port fitting head 776 may include any number of ports or fittings, and as illustrated in FIG. 7, the exemplary multi-port fitting head 776 includes a first fitting 780 and a second fitting 781. Such fittings may be any type of fittings known in the art and may be configured to removably attach to any component known in the art. For example, in some embodiments, the fittings may be luer or screw type fittings, which may be configured to attach to, for example, commonly used IV tubes or syringes. In other embodiments, the fittings may be configured to attach directly to other medical devices such as, but not limited to, endoscopes. In still other embodiments, the fittings may be simple pressure fittings or other tube connectors.

The multi-port introducer 76 may be designed to be implanted into a patient in the same way as a typical angiocatheter such as the angiocatheter illustrated in FIG. 1. Therefore, the multi-port introducer 76 may include a number of peripheral parts that are present when the introducer is packaged but that can be removed after insertion into a blood vessel. For example, in certain embodiments, the multi-port introducer 76 may include a cap 782 designed to operably connect to and close off the second fitting 781, and a cap 783 designed to operably connect to and close off the first fitting 780. In particular embodiments, the multi-port introducer 76 may include a needle assembly 78 sized and configured to be received within a lumen of the multi-port introducer 76. The needle assembly may generally include a needle 784 sized such that the distal pointed end 786 of the needle extends beyond the tapered distal end 774 of the introducer tube 772 when the needle 784 is received in the multi-port introducer 76. The needle assembly 78 may further include a fitting or stopper 788 designed and configured to operably connect to at least a portion of the multi-port introducer 76 and hold the needle in place within the multi-port introducer 76. In some embodiments, the fitting or stopper 788 may be held in place using simple pressure fittings, and in other embodiments, the fitting or stopper 788 may include a luer or screw-type fitting used to hold the needle assembly 78 in place during insertion into the blood vessel. In operation, the needle assembly 78 may provide sharp edges for facilitating entry into the blood vessel and through the skin. After the multi-port introducer 76 has been introduced into the blood vessel, the needle assembly may be removed leaving the multi-port introducer 76 in the blood vessel and providing an entry point into the blood vessel and circulatory system.

The first and second fittings 780, 781 may be initially covered using caps such as the cap 782, 783 shown in FIG. 7, and various common connectors may be used to connect the multi-port introducer to, for example, IV tubing or other medical devices. Therefore, a multi-port introducer may be used for introduction of fluids, medicaments, drugs, active agents, nutrients, and other fluids like a common angiocatheter.

Figure 8:
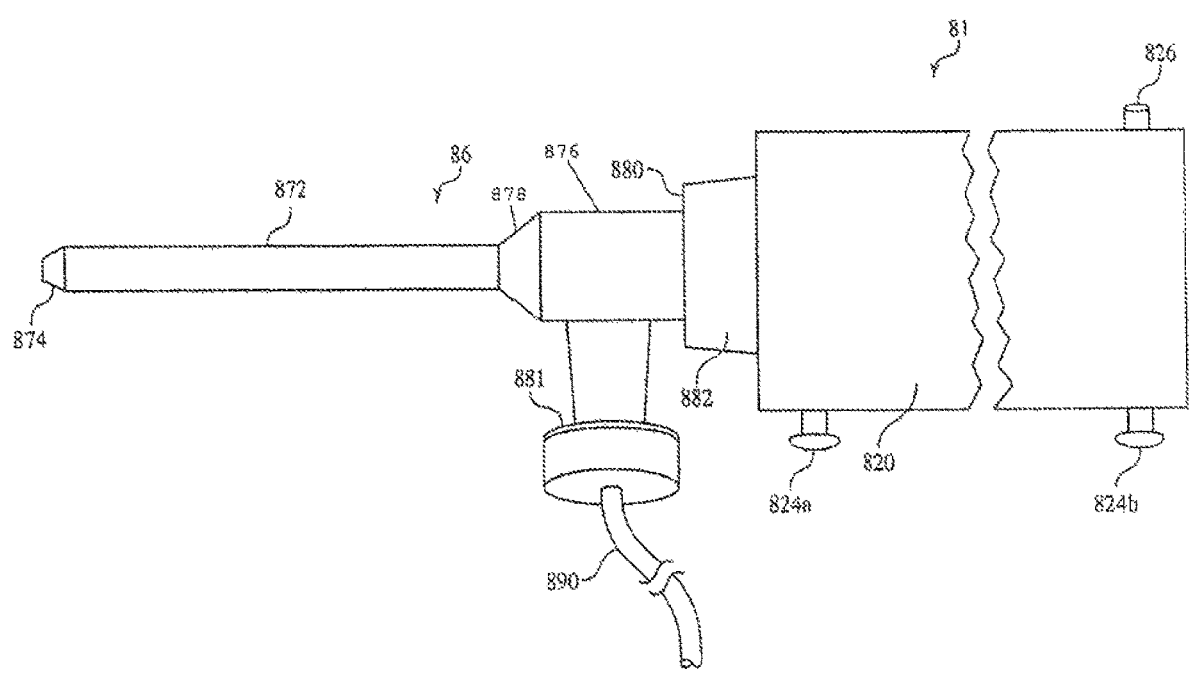
FIG. 8 is an illustration of a multi-port introducer connected to a catheter retention device.

In particular embodiments, as illustrated in FIG. 8, the multi-port introducer 86 may be designed to link to a catheter retaining device 81 such as those described herein. For example, in some embodiments, the second fitting 881 may be a luer or screw type fitting capable of attaching to a fluid source or tubing associated with a fluid source 890, and the first fitting 880 may be configured to removably attach to a catheter retaining device 81. The catheter retaining device may include any of the elements described herein and can associate with the multi-port introducer 86 through a distal fitting 822. The catheter retention body 820 may house a catheter which is wound, coiled, folded, or otherwise retained in the catheter retention body 820, such that a distal end of the catheter may enter the multi-port introducer 86 through the first fitting 880 and enter a blood vessel through the tapered distal end 874 of the introducer tube 872. The catheter may be carried into and through the blood vessel by fluid introduced into multi-port introducer the second fitting 881.

Alternatively, the fitting 880 may be fitted with a "Y" fitting. A catheter may be inserted through one of the ports and the other can be used for delivering drugs as subsequently needed. In addition, the second Y-port could be used for insertion of another catheter with a similar or different length for injection of different fluids. Multiple Y-ports can be used as needed provided that the catheters are small enough to fit through the introducer. This has the benefit of being able to provide an additional lumen without having to make another IV stick in the patient or remove and existing catheter and introduce a new one.

In some embodiments, fluid flow from the second fitting 881 of the multi-port introducer 86 may be sufficient to carry the catheter into and through the blood vessel without introducing additional fluid through other ports. In other embodiments, the catheter retaining device 81 may include one or more fittings capable of attaching to a fluid source and providing additional fluid that will flow through the catheter retaining device 81 and multi-port introducer 86 to carry the catheter into the blood vessel. For example, in some embodiments, catheter retaining device 81 may include one or more distal lateral fittings 824a and one or more proximal lateral fittings 824b through which fluid may enter the catheter retention body before flowing into the multi-port introducer 86 and into the blood vessel. The catheter retaining device 81 may further include one or more purge vents 826 for releasing air trapped in the catheter retention body 820.

The at least one portion of the multi-port introducer 86 may, generally, be sized to hold the catheter in place after deployment and may provide a seal around the outer circumference of the catheter to block flow of blood or other fluids from the introducer tube 872 into the catheter. For example, a seal may be provided at a junction between the introducer tube 872 and the Venturi feature 878 or the multi-port fitting head 876. The proximal end of the catheter may remain in a portion of the first fitting 880 such that the proximal open end of the catheter can be accessed through the first fitting 880. In some embodiments, the first fitting 880 may be configured to hold the proximal end of the catheter in a space within the first fitting 880. For example, in certain embodiments, the first fitting 880 may include a conical or spherical cavity at a proximal end of the fitting sized to receive and hold an end of the catheter. A clamp or other means for holding the catheter in the cavity may be provided at a distal end of the cavity to hold the proximal end of the catheter in place within the cavity while allowing the lumen of the catheter to remain free from obstruction. In some embodiments, the clamp may be a manual clamp. In operation, the catheter may be deployed from a catheter retention device through a multi-port introducer and into a blood vessel, and a clamp on the multi-port introducer may be engaged to fixedly hold the catheter in the multi-port injector. The catheter retention device may then be removed from the multi-port introducer with a length of catheter remaining in the catheter retention device, and the catheter may be cut near the multi-port introducer freeing the catheter retention device while leaving the catheter in place for the administration of medical fluids. Alternatively, the extra length of catheter may be coiled and attached to the patient's limb or body, or may be retained in the catheter retention device and the catheter retention device is attached securely and sterilely to the patient's limb or body.

In certain embodiments as illustrated in FIG. 7, the first fitting 780 may further include a cap 783 configured to seal the first fitting 780 and eliminate fluid flow through release of fluid from the multi-port introducer 76 after the catheter has been deployed. The cap 783 may be placed or replaced over the catheter after it has been deployed to protect the catheter from contamination when not in use. In such embodiments, the catheter may be deployed using the catheter retention device, and the catheter retention device can be removed while the catheter remains deployed in the blood vessel.

In particular embodiments, the multi-port introducer may be configured to be removed from the blood vessel following deployment of the catheter. For example, in some embodiments, the introducer tube of the multi-port introducer may be splittable such that following deployment of the catheter, the introducer tube may be removed by breaking the introducer tube along a longitudinal axis and removing the remaining halves from the insertion site. In such embodiments, the multi-port fitting head may remain associated with and/or attached to the catheter. In some embodiments, the catheter retention body may be attached to the multi-port fitting head, and in other embodiments, the catheter retention body may be removed before or after the introducer tube is removed.

In those embodiments where the introducer remains in the body, the distal end in the vessel through which the more distally deployed catheter exits is an important aspect of the present disclosure. If the introducer is a standard angiocatheter, the catheter is a relatively stiff material and the distal opening of the angiocatheter is of a relatively fixed diameter. This means that fluid can be injected around the catheter, and that there is the possibility for clot formation over time. Alternatively, the introducer or distal end of the introducer of this present disclosure can be made of silicone or other relatively elastomeric material such that it is opened by the flow of fluid to transmit the catheter distally, and then closed to seal against the outer diameter of the catheter when flow is absent. By closing to reduce or eliminate the ingress of blood, the likelihood of clot formation in the introducer lumen is significantly reduced. To inject fluids through the introducer and into the patient, applying sufficient pressure will expand the introducer and conduct the fluid into the patient's vessel. Alternatively, slits or other openings may be provided in the wall of the introducer to transmit the injected fluid into the patient's vessels.

The multi-port introducers of various embodiments may include any number of additional features provided to facilitate ease of use or provide improved control of fluid flow through either the introducer tube or a catheter extending through the multi-port introducer. For example, in some embodiments, the introducer tube may include one or more discharge ports 990 that can be adjusted using a discharge button 991 located on a more distal portion of the multi-port introducer 96. The discharge port 990 may, generally, be one or more lateral openings such as longitudinally adjustable slits or variable window apertures that are positioned on a portion of the introducer tube 972. The discharge button 991 may twist or slide to be activated and may increase the flow of fluid into the blood vessel by allowing fluid from the multi-port introducer 96 to exit through the discharge ports 990 while simultaneously reducing the amount of fluid passing over the catheter thus slowing the deployment rate of the catheter.

In some embodiments, the multi-port fluid port may further include a compression brake and adjustable iris located between the first fitting and the introducer tube designed and configured to contact the catheter and slow the rate of deployment by way of friction as the catheter is deployed by depressing the brake or iris. The Venturi iris can be constructed to either compress inward or rotate around the body of the catheter. When activated, the opening of the Venturi iris widens and reduces the pressure drop between the inflow and out flow regions and reducing the force by the fluid flow applied to the catheter.

The various portions of the devices described above, including the angiocatheter or multi-port introducer and the catheter retaining device may be combined to provide a single device, or in some embodiments, each element may be separate devices that are assembled during use. In other embodiments, the various components may be combined in a kit including one or more angiocatheters, one or more multi-port introducers, one or more catheter retaining devices, fittings, tubing, and other components that may be useful for introducing a catheter into a blood vessel using the devices described above, and any combination of such components. As mentioned above, in various embodiments, the catheter may be pre-assembled, sterilized, and sealed in the catheter retention body of the catheter retaining device. The catheter can remain inside a sterile container or package until it is inserted into the patient, so that the sterile field need not be much larger than that of a simple IV catheter (which typically involves just washing around the introduction site).

In some embodiments, the catheter may be processed before being packaged into the catheter retention body or the catheter may be packaged with additional components that may ease introduction of the catheter or provide other improvements. For example, in certain embodiments, a lubricant may be included in the sterile packaging to reduce any potential friction during deployment of the catheters. Similarly, a coating designed to reduce friction during deployment may be applied to the catheters during or prior to packaging.

Various embodiments are directed to methods for deploying a catheter. In general such methods include introducing a catheter into a blood vessel at an introduction site and simultaneously introducing a fluid into the blood vessel at the introduction site. In certain embodiments, simultaneously introducing of the catheter and fluid at a common introduction site can be carried out using a multi-port introducer such as those described above. In other embodiments, a multi-port introducer and a catheter retaining device or a catheter retaining device and a common angiocatheter can be used to simultaneously introduce a catheter and fluid into a blood vessel at a common introduction site. Without wishing to be bound by theory, the introduction of fluid with the catheter may allow the catheter to be carried through a blood vessel with the flow of blood through the blood vessels to the deployment site where it can be used for the deployment of drugs or other medical fluids without providing an external pushing force. The fluid flowing into the blood vessel may increase the blood volume and enlarge or distend the blood vessels to improve blood flow and assist in movement of the catheter through the blood vessels. Therefore, embodiments of the methods may be used for deployment of catheters through veins, which generally exhibit weaker blood flow, as well as arteries, and in certain embodiments, the methods may be directed specifically to introducing a catheter into a vein.

The flow rate and volume of fluid introduced during delivery of the catheter may vary among embodiments and may depend on various factors including, for example, restraining forces, the size of the catheter, the distance from the insertion site the catheter must travel for proper placement, the size of the vessels, amount of flex or expansion desired by the walls of the vein into which the catheter is being introduced, and the like and combinations thereof. In general, the flow rate should be sufficient to urge the catheter through the patient's vein and through any insertion apparatus such as an angiocatheter, a multi-port introducer, or either an angiocatheter or a multi-port introducer and a catheter retaining device. In some embodiments, the flow rate may be sufficient to enlarge or distend the blood vessel, which may facilitate insertion of the catheter into the blood vessel, and in further embodiments, the flow rate may be sufficient to augment the flow of the blood in the blood vessel. For example, the flow rate may be faster than the flow of blood such that that the flow of fluid from the insertion apparatus creates or augments the forward or distally directed force on the catheter.

The flow rate may further off set restraining forces. As used herein, "restraining force" may be any force that slows or could slow movement of the catheter into the blood vessel. For example, restraining forces can be created by the friction as the catheter moves through an insertion apparatus such as an angiocatheter, a multi-port introducer, or either an angiocatheter or a multi-port introducer and a catheter retaining device. Restriction forces further include manual restraint of the catheter caused by friction as the catheter is removed from a storage container or uncoiled from a spool. Limiting the play out of catheter, for example, a motion controlled or motion limited spool can also be considered a source of restraining force. Still other sources of restraining force include handling of the catheter by the clinician as it is introduced into the insertion apparatus. Further sources of restraining forces include for example, pinch clamps or friction wheels.

In some embodiments in which the catheter is deployed through an angiocatheter or a multi-port introducer, the angiocatheter or multi-port introducer may be removed from the insertion site after deployment. In other embodiments, the angiocatheter or multi-port introducer head may remain inserted into the blood vessel after deployment and may continue to be used for delivery of fluids into the blood vessel. For example, in some embodiments, methods may include the steps of introducing or deploying a catheter into a blood vessel through an angiocatheter or multi-port introducer and introducing fluid through the angiocatheter or multi-port introducer after deployment of the catheter. In some embodiments, the fluid introduced into the blood vessel after deployment may be saline, nutrient fluids such as glucose, or other medical fluid that can be continually introduced into a patient. In other embodiments, the angiocatheter or multi-port introducer may be used for locally delivering fluids such as, for example, contrasting agents for scans or other tests, or drugs or other active agents, or combinations of these with saline or other medical fluids. In certain embodiments, anti-fibrotic agents may be administered through the angiocatheter or multi-port introducer, and the anti-fibrotic agent may wash over the catheter mitigating the fibrotic response and reducing fibrous tissue deposits on the external surface of the catheter to reduce thrombosis or catheter occlusion. Therefore, the catheter may remain in place for a longer period of time than catheters that do not remain associated with an angiocatheter or multi-port introducer that allows for fluid to be introduced at an insertion site while a catheter is in place at the insertion site.

More particular embodiments include the steps of inserting an angiocatheter or multi-port introducer into a blood vessel, and in some embodiments, securing the angiocatheter or multi-port introducer using standard means such as taping to the patient's skin with medical tape. The method may include connecting the angiocatheter or multi-port introducer to a fluid source and providing a flow of fluid through the angiocatheter or multi-port introducer. Providing fluid flow may be accomplished by any means. For example, in some embodiments, fluid flow may be provided using saline from an IV bag and associated tubing that relies on gravity. In other embodiments, fluid flow may be provided by a pump that pushes or pumps fluid from a reservoir through the angiocatheter or multi-port introducer. In still other embodiments, flow of fluid may be provided using a syringe or other manual device. A catheter may then be inserted into the angiocatheter or multi-port introducer while simultaneous fluid flow is maintained through the angiocatheter or multi-port introducer. The catheter is carried by the flow of fluid through the angiocatheter or multi-port introducer and through the blood vessels by the fluid flow.

In some embodiments, the step of inserting a catheter into the angiocatheter or multi-port introducer can be facilitated with a catheter retention device such as those described above. In such embodiments, after inserting the angiocatheter or multi-port introducer into the blood vessel, the method may include attaching a catheter retaining device housing a catheter to the angiocatheter or multi-port introducer and initiating a flow of fluid through the angiocatheter or multi-port introducer, the catheter retention body, or both. The flow of fluid may then carry the catheter into the blood vessel effecting deployment of the catheter.

In certain embodiments, the catheter retaining device may include a number of fittings or purge vents. Referring to the catheter retention device of FIG. 3A, for example, such methods may include operably connecting the catheter retaining device 31 to the angiocatheter or multi-port introducer, opening a purge vent 327 on a catheter retention body 320, and filling the catheter retention body 320 with fluid. As fluid is introduced into the catheter retention body 320, air from inside the catheter retention body 320 can be pushed out through the purge vent 327 thereby removing air from the catheter retention body 320. When fluid begins flowing through the purge vent 327, the purge vent 327 may be closed, and further fluid introduced into the catheter retention body 320 can flow into the angiocatheter or multi-port introducer carrying the catheter from the catheter retention body 320 into the angiocatheter or multi-port introducer and into the blood vessel. In some embodiments, deployment of the catheter may stop when the bulge or stopper associated with a proximal end of the catheter reaches a position on the catheter retaining device, angiocatheter, or multi-port introducer that cannot allow the bulge or stopper to pass.

After deployment of the catheter, the catheter retaining device may be removed from the angiocatheter or multi-port introducer, and in some embodiments, the catheter may be secured to the angiocatheter or multi-port introducer using a cap. The catheter may be accessed as necessary by removing the cap or attaching a delivery device through the cap. As discussed above, fluids such as saline, active agents, drugs, or contrast agents can be introduced into the patient through the catheter while the angiocatheter or multi-port introducer remains in place, and saline, active agents, drugs, or contrast agents can be introduced into the blood vessel through the angiocatheter or multi-port introducer while the catheter remains in place. In various embodiments, the catheter may be sized to be positioned at a specific location within the body of the patient such as near a particular organ or injury, for example, near the patient's heart to effectuate localized delivery of the active agent, drug, or contrast agent introduced through the second catheter.

Figure 9:
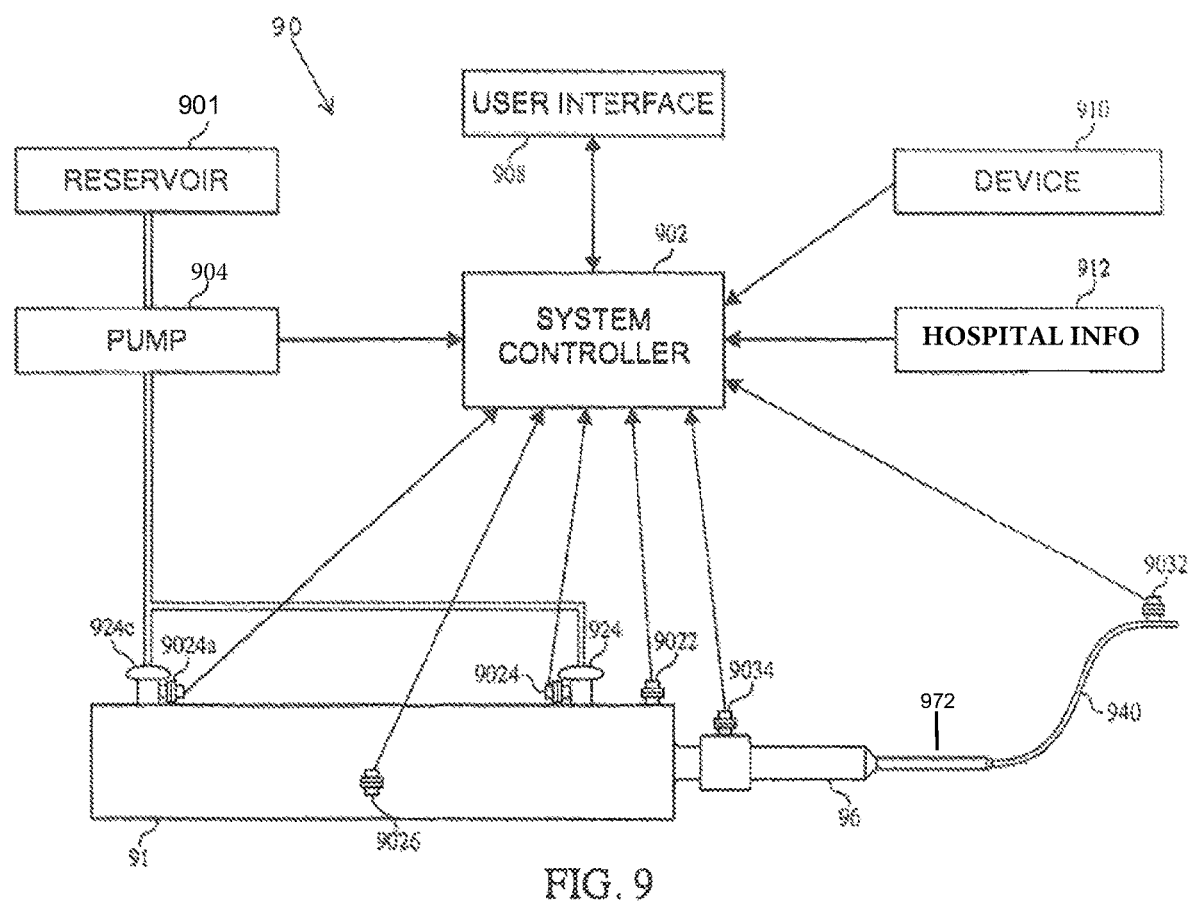
FIG. 9 is a schematic diagram showing an exemplary control system for deploying a catheter.

While the catheter and deployment system described herein can be operated manually using existing discrete ancillary devices and equipment such as angiocatheters, ultrasound imagers, and hand held syringes with saline, there can be a benefit in standardization of care and ease of use that comes with using an integrated electromechanical system. FIG. 9 shows a system that can be used to deploy the catheters of various embodiments. Such systems 90 may include, for example, a system controller 902, electronically connected to one or more pumps 904 that can be fluidly connected to a fluid reservoir 906 or other source of injectable fluid. The system controller 902 may be configured to receive information about the catheter 940, catheter retention body 91, and insertion device, the patient, the procedure, and other parameters to determine the volumes and flow rates to be delivered over time. In addition, the system controller 902 may receive information from a user interface 908, information tags on devices connected to the system controller such as RFID tags or bar codes 910, Wi-Fi or other internet links to hospital information systems 912, or combinations thereof.

In some embodiments, information about the catheter, catheter retention body, and insertion device, the patient, the procedure, and other parameters may be received by the control system 902. For example, the control system 902 may be operably connected to the catheter retention body 91 through one or more catheter play-out monitors 9022, one or more flow port monitors 9024 associated with fluid ports 924, pressure sensors 9026 on an inner surface of the catheter retention body 91, and like and combinations thereof. In some embodiments, the system 90 may further include a tip location monitor 9032 or measurement system 9034 associated with the catheter 940. A wide variety of tip location methods are currently used and can be incorporated into the systems of embodiments. In certain embodiments, the system 90 may use information received from a play-out monitor 9022 or measuring device 9034 and a tip location monitor 9032 to control the fluid flow by modulating the pump 904 or operating friction augmentation devices on the catheter retention body 91. The information may be used by the operator and/or a computer program to optimize the tip location. In some embodiments, the tip location can be verified via a method such as a chest X-ray following deployment, and the tip location can be adjusted using the system if the deployment system 90 has not been removed. Alternatively, the catheter can be pulled back or moved forward if sterility has been maintained.

It will be appreciated that various of the above-disclosed and other features and functions, or alternatives thereof, may be desirably combined into many other different systems or applications. It will also be appreciated that various presently unforeseen or unanticipated alternatives, modifications, variations or improvements therein may be subsequently made by those skilled in the art which are also intended to be encompassed by the disclosed embodiments. If not otherwise stated herein, it may be assumed that all components and/or processes described heretofore may, if appropriate, be considered to be interchangeable with similar components and/or processes disclosed elsewhere in the specification, unless an express indication is made to the contrary.

What is claimed is:

1. A peripherally inserted central catheter comprising:
    a proximal end and a distal end;
    a single lumen extending from the proximal end to the distal end of the catheter;
    at least one distal opening in the single lumen positioned at or near the distal end; and
    at least one proximal opening in the single lumen positioned at or near the proximal end,
    wherein the at least one proximal opening is configured to open under a first pressure and a first flow rate generated during a power injection, but to not open under a second pressure and a second flow rate generated during a blood sampling process or when drugs are infused through the at least one distal opening, wherein the first pressure is a pressure of 100 psi up to 350 psi and the second pressure is a pressure of 10 psi to 100 psi, wherein the catheter is configured for insertion into a peripheral circulatory system of a patient to extend into a central circulatory system of the patient, wherein the at least one proximal opening and the at least one distal opening are separated by a distance so that, when the catheter is placed through the peripheral circulatory system to extend into the central circulatory system, the catheter is configured to deliver at least a first fluid through the at least one distal opening to the central circulatory system near a heart of the patient at the second pressure and the second flow rate and is configured to deliver at least a second fluid through the at least one proximal opening to the peripheral circulatory system in an arm of the patient at the first pressure and the first flow rate, and wherein, during insertion of the catheter through the peripheral circulatory system toward the central circulatory system, the catheter is configured to deliver at least the second fluid at the first pressure and the first flow rate through the at least one proximal opening is configured to increase an overall flow rate through a blood vessel at the distal end to direct at least the second fluid to carry the distal end toward the central circulatory system.

2. The catheter of claim 1, wherein the first fluid is the same as the second fluid.

3. The catheter of claim 1, wherein the first fluid is administered sequentially to the second fluid.

4. The catheter of claim 1, wherein at least one of the at least one proximal opening and the at least one distal opening comprise at least one proximal slit and at least one distal slit.

5. The catheter of claim 1, wherein the at least one distal opening is biased to a closed position and configured so that a fluid pressure within the catheter created when the distal opening is closed stiffens the catheter to reduce or eliminate undulating, flapping or whipping of the catheter during deployment of the catheter.

6. The catheter of claim 1, wherein the catheter is composed of a single material and the proximal end of the catheter has a wall thickness greater than a wall thickness of the distal end of the catheter; or wherein the proximal end of the catheter is composed of a first material and the distal end of the catheter is composed of a second material, such that the proximal end is configured to withstand the first pressure and the distal end is configured to withstand the second pressure.

7. The catheter of claim 1, wherein the first fluid is a first active agent, and the second fluid is selected from a group consisting of a second active agent, saline, a medical fluid, a contrast agent, and combinations of any thereof.

8. The catheter of claim 1, further comprising additional lateral openings positioned at one or more positions throughout a length of the catheter to release a medical fluid over the length of the catheter.

9. A multi-lumen catheter comprising:
a proximal end and a distal end; and
a first lumen and at least a second lumen, wherein the first lumen comprises at least one distal opening positioned at or near the distal end of the catheter and the second lumen comprises at least one proximal opening positioned near the proximal end of the catheter, wherein the catheter is configured for insertion into a peripheral circulatory system of a patient to extent into a central circulatory system of the patient, wherein the at least one distal opening of the first lumen is configured to open under a first pressure of up to 100 psi and the at least one proximal opening of the second lumen is configured to open under a second pressure of 100 psi to 350 psi, wherein the at least one proximal opening and the at least one distal opening are separated by a distance so that, when the catheter is placed through the peripheral circulatory system to extend into the central circulatory system, the catheter is configured to deliver at least a first fluid through the at least one distal opening to the central circulatory system near a heart of the patient at the second pressure and is configured to deliver at least a second fluid through the at least one proximal opening to the peripheral circulatory system in the patient at the first pressure, and wherein, during insertion of the catheter through the peripheral circulatory system toward the central circulatory system, the catheter is configured to deliver at least the second fluid at the first pressure and a first flow rate through the at least one proximal opening is configured to increase an overall flow rate through a blood vessel at the distal end to direct at least the second fluid to carry the distal end toward the central circulatory system.

10. The catheter of claim 9, wherein the second lumen is shorter in a longitudinal direction than the first lumen, wherein the longitudinal direction is from the proximal end to the distal end of the catheter.

11. The catheter of claim 10, wherein a portion of a circumferential wall around the first lumen is located within the second lumen.

12. The catheter of claim 11, wherein the circumferential wall around the first lumen is laterally movable within the second lumen.

13. The catheter of claim 11, wherein the second lumen is a lumen of a catheter introducer.

14. The catheter of claim 13, further comprising a Venturi feature within the catheter introducer.

15. The catheter of claim 9, wherein a circumferential wall of the second lumen is stiffer than a circumferential wall of the first lumen.

16. The catheter of claim 9, wherein a fluid pressure within one or both of the first lumen and the second lumen force at least one opening to open allowing fluid to exit one or both of the first lumen and the second lumen, and wherein a decrease of the fluid pressure within the respective first lumen and the second lumen cause the at least one opening to close.

17. The catheter of claim 9, wherein the second fluid is saline or a medical fluid introduced to the blood vessel through the at least one proximal opening and wherein the second fluid causes at least one of enhanced fluid flow in the blood vessel or expansion of the blood vessel which assists movement of the distal end of the catheter through the blood vessel to a final deployment site.

* * * * *